United States Patent [19]
Bruno

[11] Patent Number: 5,464,766
[45] Date of Patent: Nov. 7, 1995

[54] MULTIENZYME POWDERED COMPOSITION CONTAINING BACTERIA FOR TREATMENT OF WASTE

[75] Inventor: Mark Bruno, Raleigh, N.C.

[73] Assignee: Enzyme Research & Development Corporation, Gilberts, Ill.

[21] Appl. No.: 222,108

[22] Filed: Apr. 4, 1994

[51] Int. Cl.$^6$ .............................. C12N 9/00; C12N 9/96; C02F 1/00
[52] U.S. Cl. .................. 435/187; 210/601; 210/632; 435/188; 435/220; 435/262.5; 435/183; 435/252.5
[58] Field of Search ..................... 435/183, 187, 435/188, 220, 252.5, 262.5; 210/601, 632

[56] References Cited

U.S. PATENT DOCUMENTS

| | | | |
|---|---|---|---|
| 3,915,853 | 10/1975 | Luck | 210/11 |
| 3,983,002 | 9/1976 | Ohya et al. | 195/66 |
| 5,238,833 | 8/1993 | Sanders et al. | 435/172.3 |

Primary Examiner—David M. Naff
Assistant Examiner—Deborah K. Ware
Attorney, Agent, or Firm—Thomas W. Tolpin

[57] ABSTRACT

A stabilized dust-free powdered enzyme/bacterial fermentation product is provided for readily treating drains, septic tanks, distribution boxes, holding tanks, drain fields, sewer lines, dry wells, grease traps, compost heaps, and garbage disposals. The stabilized powdered formulation effectively digests and liquifies most organic wastes flushed into on-site waste disposal systems. The environmentally attractive product can also be used for regular periodic sludge pumpouts. The waste-digesting composition can include: enzymes, enzyme preservatives, enzyme activators, non-pathogenic aerobic and anaerobic bacteria, bacterial nutrients, buffers, emulsifiers, and heavy metal scavengers. In a preferred embodiment the composition contains multiple enzymes having less than 26% by weight of the total weight of the composition, and specifically 0.1% to 15% protease, 0.1% to 15% amylase, 0.1% to 15% cellulase, 0.1% to 15% lipase, 0.1% to 15% Bacillus species, 0.1% to 20% phosphate-containing buffer compounds, such as monosodium phosphate, 1% to 20% enzyme preservative, and 0.1% to 10% ion scavenger compounds, as well as 50% to 95% dendritic salts also providing a buffering effect for the composition.

7 Claims, No Drawings

MULTIENZYME POWDERED COMPOSITION CONTAINING BACTERIA FOR TREATMENT OF WASTE

BACKGROUND OF THE INVENTION

This invention pertains to waste treatment, and more particularly, to an enzyme composition for treating waste in septic tanks and other places.

Solid waste buildup in septic systems causes large numbers of septic failures. Clogged household plumbing and grease traps cause backup, blockage and slow running drainpipes. In the commercial sector, there is a need to help move solid waste through the waste treatment process more efficiently and effectively.

Waste digestion compositions have been used in the past for both commercial and home use. These compositions fell far short with respect to initial effectiveness as well as long-lasting efficacy. The very first of these was a simple cake of yeast. Although being a saprophytic microbe, it was almost completely useless. Yeasts digest only carbohydrates which represent less than five percent of the solids in a septic tank.

Other saprophytic microbes have been utilized in septic tank cleanup, such as aerobes at the stage of high oxygenation, or anaerobes at the stage of no oxygenation. Although proving effective over long periods of usage, difficulty in establishing sufficient populations gave rise to long spans of time from the time the microbe product was added to the system to the time they established themselves as normal flora.

Homeowners have tried the addition of large amounts of acids, lye or caustic compounds. This may temporarily burn away some of the clogging material, but the ultimate result is damaging. Such chemicals kill bacteria on contact, and that puts an end to their liquefying process that septic tanks and cesspools depend on. Furthermore, this procedure loosens chunks of solids that can flow into the drainage pipes and cause blockage. Caustics also kill ground organisms that become useless in the job of purifying the seeping effluent. Caustics change soil structure, breaking down the soil into finer particles that pack together, reducing the ability of the septic tank or cesspool effluent to seep into the soil. When the bacteria within a septic tank or cesspool are abused or destroyed, a decrease occurs in the digestive and liquefaction ability of organic material that the household flushes into the waste disposal system. The solids rise to a point that blocks the inlet-outlet pipes. When these pipes get clogged, the waste material of the household cannot be flushed out. Sinks, tubs, and toilets backup and overflow occurs.

Enzymes have found many uses in modern industry, such as: processing textiles and paper coatings, wine and fruit juice production, converting corn syrup into fructose to double its sweetness, separating pectins from apple juice, conversions of starch to sugars to alcohol to vinegar, and lactic acid production.

Prior enzyme compositions for sewage treatment contained 15% by weight, ground corn cob filler that proved to be most detrimental to septic systems by compounding the problem the formulation was developed to alleviate. Corn cob filler also tended to clog septic tanks and drains. Prior enzyme compositions also contained at least 26% by weight enzymes, which is an excessive amount of enzymes. It was thought that a greater concentration of enzyme would produce a more efficacious product with the high corn cob filler content. This proved not to be the case and eventually too cost prohibitive.

It is, therefore, desirable to provide an improved composition for use in waste treatment, which overcomes most, if not all, of the preceding problems.

SUMMARY OF THE INVENTION

An improved waste treatment composition comprising a special enzyme/bacterial formulation is provided to safely, efficiently and easily treat human and animal waste, as well as other types of waste. Advantageously, the novel composition is economical, reliable and effective.

The enzyme/bacterial composition of the invention can be used to digest waste in a wide variety of application points depending on where the problem is occurring. These application points include: septic tanks, grease traps, drains, drain fields, recreational vehicle (RV) holding tanks, garbage disposals and farms. The novel composition is also useful to clean sinks and drains clogged with human or animal hair, as well as for urinals and toilet flushing.

The enzyme/bacterial composition comprises bacterial cultures blended with special enzymes to exhibit an initial shock of activity followed by a longer lasting effect of waste digestion. The composition contains nonpathogenic aerobic and anaerobic bacteria in conjunction with four or preferably five enzymes: amylase, cellulase, lipase, pectinase and protease. The enzymes, as described, are the components which exhibit the initial jolt of activity to the system with sustained activity accomplished by the bacterial component.

Through the use of the invention, a natural and sustained aide to the normal operation of a waste disposal system can increase its capacity for waste elimination. By substantially reducing grease, gum and pectins which cause glazing of drainfields, drainage pits and distribution boxes, it eliminates soggy soil and puddling due to clogging.

The specially blended composition ensures maximum results at the lowest cost in the shortest period of time. Each ingredient is functional and contributes to the invention's effectiveness. The novel composition is nonpoisonous, noncorrosive, noncaustic and ecologically advantageous. It works where bacterial products alone will not because it contains the enzymes mentioned above to start the process.

The use of more sophisticated enzymes and substrate specific enzymes in waste digestion and especially in a typical home septic tank, is very desirable. A combination of amylase, cellulase, lipase, and protease is especially useful. The addition of pectinase is also desirable for many types of waste cleanup. These compositions yielded a very strong initial surge of activity but at the same time exhibited no long-lasting adverse effect.

The inventive composition is useful for treating sewage and organic waste, such as in septic tanks, garbage disposals, drains, drainage fields, grease traps and other waste disposal sites. To this end, the inventive composition comprises bacterial culture and a multiple enzyme package without corn cob fillers. The multiple enzyme package comprises substantially less than 26% by weight of the total weight of the composition, preferably about 1.5% of the total weight of the composition. Specifically, the inventive multiple enzyme package comprises protease, amylase, cellulase, and lipase, with the optional addition of pectinase for some types of waste treatment. Preferably, the waste digesting composition includes: a bacterial nutrient, an enzyme activator, an enzyme preservative, an emulsifier, at least one buffer, and a scavenger to deactivate chlorine and heavy metals.

Multi-purpose compounds can be used in the waste digesting composition to serve more than one function. For example, dendritic salt can be used as a buffer and an enzyme preservative to increase the useful shelf life of the enzymes in the composition. Disodium phosphate and monosodium phosphate can be used as buffers, enzyme activators and bacterial nutrients. Nonylphenoldecylethoxylate, such as sold under the brand name of Surfonic N-95, can be used as an emulsifier and a bacterial nutrient. Multi-purpose compounds advantageously decrease the amount and cost of materials in the composition as well as raw material inventory. These savings can be passed on to the customer.

Enzymes combined with bacteria as a catalyst in the improved enzyme bacterial composition are an environmentally safe way to decrease the solid mass in any waste treatment system. The inventive composition is safe, non-hazardous, non-caustic, non-toxic and does not harm plumbing. The enzymes in the enzyme composition react with the solid waste and convert the waste into other forms of matter and energy. This process reduces septic system failures and keeps plumbing running freely. It also reduces the frequency of septic system clean outs. Solid waste is also safely reduced by the novel composition in industrial applications thereby creating an efficient disposal of waste matter and reducing the amount of water treatment needed at water treatment facilities. Desirably, the waste-digesting composition also reduces the odors in the treated disposal site.

The inventive technology has produced unexpected surprisingly good results. Tests show the technology to be very useful for cleanup of septic tanks, drains, drainage field, garbage disposals, grease traps, and sludge pumps.

A more detailed explanation of the invention is found in the following description and appended claims.

DETAILED DESCRIPTION OF THE PREFERRED EMBODIMENTS

The inventive Tetrazyme, also referred to as Tetrazyme PC-108NV, is a multiple enzyme waste-digesting composition and waste treatment formulation for treating sewage and waste. Tetrazyme provides a combination of bacteria and enzymes in composition to yield an initial surge of digestive activity which maintains its efficacy over extended periods of time with normal use.

Tetrazyme is a stable powdered multi-enzyme and non pathogenic bacterial formulation which treats, reduces and/ or oxidizes virtually all organic wastes found in most on site sewage disposal systems. Tetrazyme cleans and maintain drains, septic tanks, distribution boxes, holding tanks, drain fields, dry wells, grease traps and garbage disposals. An important purpose for applying Tetrazyme into plumbing and on site sewage waste treatment systems is: the conversion of proteins to amino acids; fats to fatty acids, glycerides and subsequently to triacetin which inturn is converted to acetic acid; cellulosics into starches; and starches into carbon reducing sugars. The end products of these hydrolytic reactions are food for the flora normally found in the ecologically acceptable remineralization of waste.

The formulation of Tetrazyme can include: enzymes, enzyme preservatives, enzyme activators, saprophytic bacteria, bacteria nutrients, buffers, emulsifiers, and heavy metal scavengers. The enzymes can include: amylase, cellulase, protease, lipase, and pectinase Specifically, Tetrazyme comprises by weight: 50% to 95% buffering salts; 0.1% to 15% protease; 0.1% to 15% amylase; 0.1% to 15% cellulase; 0.1% to 15% lipase; 0% to 15% pectinase; and 0.1% to 15% saprophytic bacteria. Preferably, the buffering salts comprise by weight: 50% to 95% dendritic salt, 1% to 20% disodium phosphate; and 1% to about 20% monosodium phosphate. At least 0.1% to 15% pectinase can be used for some types of waste cleanup. The composition can include 1% to 20% of an non-ionic enzyme preservative. The composition can also include 0.1% to of an adverse affecting ion scavenger, preferably sodium thiosulfate.

In the preferred form, Tetrazyme comprises by weight: 60% to 90% dendritic salt; 0.1% to 5% protease; 0.1% to 5% amylase; 0.1% to 5% cellulase; 0.1% to 5% lipase; 0% to 5% pectinase; 1% to 10% ionic enzyme preservative; 1% to 10% disodium phosphate; 1% to 10% monosodium phosphate; 0% to 10% sodium thiosulfate; and 1% to 5% nonpathogenic bacteria comprising aerobic bacteria and/or anaerobic bacteria. For some types of waste treatment, the most preferred composition includes 0.1% to 5% pectinase. The composition can also include at least 0.1% sodium thiosulfate, and preferably 1% to 2% sodium thiosulfate.

Most preferably, for best results, Tetrazyme comprises by weight: at least about 70% dendritic salt comprising sodium chloride; 0.25% to 0.5% protease; 0.35% to 0.75% amylase; 0.1% to 0.25% cellulase; 0.1% to 0.25% lipase; 0% to about 0.25% pectinase; 2% to 7% non-ionic enzyme preservative comprising Nonylphenoldecylethoxylate; 4% to 8% disodium phosphate; 2% to 4% monosodium phosphate; and 5% to 10% bacteria comprising one or more of the following: Bacillus subtilis, Bacillus licheniformis, Bacillus megaterium, and Bacillus polymyxa.

The composition of the invention is a free-flowing, dust-free powdered mixture of bacterial cultures with the addition of a mixture of enzymes to include, but not be limited to: amylase, cellulase, lipase and protease. Specific examples of the microbes to be contained in the bacterial cultures include the species of Bacillus subtilis, Bacillus licheniformis, Bacillus megaterium, and Bacillus polymyxa.

Specific examples of amylases that can be used are bacterial amylase at 200,000 BAU units/gram, fungal amylase at 100,000 SKB units/gram, Amyloglucosidase at 100 AG units/gram and bacterial amylase at 175,000 BAU/gram.

Specific examples of cellulases that can be used are fungal cellulase at 200,000 $C_1$-ase units/gram, cellulase AEI at 20,000 CMCase units/gram and cellulase trichoderma viride at 40,000 CMCase units/gram.

Specific examples of lipases that can be used are fungal lipase at 160,000 LU units/gram, candida cylindracae lipase AP at 60,000 units/gram, and lipase aspergillis niger AP at 10,000 units/gram.

Specific examples of proteases that can be used are acid stable protease at 10,000 units/gram, alkaline protease at 12,000 Anson units/gram, neutral protease at 2,000 Northrup units/gram and fungal protease at 500,000 HUT units/gram.

Specific examples of pectinase that can be used are pectinase AEI at 10,000 AJD units/gram, Pectinex 3X at 3,000 FDU units/gram, Pectinex 5X at 5,000 FDU units/ gram and Ultrazyme 100 at 400 FDU units/gram.

The concentrations or amounts of the various enzymes used in the composition depend on cost considerations and the specific application for which the composition will be used. Varying concentrations can be used depending on the system or the point in the system the composition is to be added.

The composition is preferably prepared in a manner to maintain low dust levels during mixing. Although the finished composition is dust free, component parts have the potential of creating levels of dust that may be an irritant to the respiratory tract. The use of a particulate dust mask is desirable during the mixing procedure.

Mixing is initiated by the addition of dendritic salt to a compounding ribbon mixer with the blades in motion. To this the protease is added followed immediately, through an opposite addition port, by a nonionic preservative for the enzyme such as: iso-oxtyl phenoldodecylethoxylate, nonylphenoldecylethoxylate, alpha dodecanoldecylethoxylate or alpha dodecanoldodecylethoxylate. Following this, the combination of enzymes chosen to make up the composition is added consecutively allowing approximately five to ten minutes mixing between each separate addition. The order of their addition is nonconsequential; however, they should be added separately with an intermittent mix between.

The composition has the bacterial culture added next followed by sodium or potassium containing mono or dibasic phosphate buffering salts. If desired, a fragrance can also be added as one of the last components, again noting the need for a five to ten minute mix between each component addition. After all additions have been made, a final twenty to thirty minute mix is needed before final packaging.

The composition of the invention can be used in a number of waste digestion applications. As stated above, whatever type of waste digestion system the composition uses or at which point of a septic system the composition is added to the system dictates the combination and concentration of the enzymes that comprise the composition. For example, a high lipase-containing composition is needed for grease trap and household drain maintenance, whereas a high lipase, cellulase and bacterial culture composition is more effective for septic tank maintenance. In addition, a high amylase, pectinase and bacterial culture composition is most effective in treating drainage fields where glazing due to gums and pectins is the problem.

Specific examples of the bacterial/enzyme compositions are as follows:

EXAMPLE I

| Septic Tank Cleaner | |
|---|---|
| Formulation Ingredient | Weight % |
| Dendritic Salt | 74.6 |
| Protease 1.75 M | 0.50 |
| Surfonic N-95 | 5.00 |
| Amylase 28 M | 0.50 |
| Lipase 120 K | 0.15 |
| Cellulase 240 K | 0.15 |
| Culture B C-3B | 5.00 |
| Disodium Phosphate | 8.00 |
| Monosodium Phosphate | 4.00 |
| Sodium Thiosulfate | 2.00 |
| Lemon Scent | 0.10 |

EXAMPLE II

| Grease Trap Cleaner | |
|---|---|
| Formulation Ingredient | Weight % |
| Dendritic Salt | 89.73 |
| Protease 1.75 M | 0.50 |
| Surfonic N-95 | 2.00 |

| Grease Trap Cleaner (continued) | |
|---|---|
| Formulation Ingredient | Weight % |
| Amylase 28 M | 0.39 |
| Lipase 120 K | 0.25 |
| Cellulase 240 K | 0.13 |
| Disodium Phosphate | 4.00 |
| Monosodium Phosphate | 2.00 |
| Sodium Thiosulfate | 1.00 |

EXAMPLE III

| Drainage Field Cleaner | |
|---|---|
| Formulation Ingredient | Weight % |
| Dendritic Salt | 72.85 |
| Protease 1.75 M | 0.25 |
| Surfonic N-95 | 7.00 |
| Amylase 28 M | 0.75 |
| Lipase 120 K | 0.15 |
| Cellulase 240 K | 0.25 |
| Pectinase | 0.25 |
| Culture BC-3B | 5.00 |
| Disodium Phosphate | 8.00 |
| Monosodium Phosphate | 4.00 |
| Sodium Thiosulfate | 1.00 |
| Lemon Scent | 0.50 |

Through this invention, a highly effective waste digestion composition is achieved. In the course of its application, an initial shock or surge of digestive activity is accomplished by a particular complement of enzymes. This in turn is followed by a supplement of bacterial cultures whose specific metabolic requirements meet the demands of continued waste digestion over longer periods of time.

Sewage

Generally there are five generic organic substances that comprise 95% to 98% of all organic waste carried to and through on site sewage disposal systems.

Amylases: Carbohydrates, such as in potatoes, flour, bread, cakes, starch, vegetable, vegetable, fruit, grain pulp and nut meats.

Lipids: One of a class of compounds which contain long chain aliphatic hydrocarbons and other derivatives, such as fatty acids, alcohols, amines, amino alcohols, and aldehydes. Lipids includes waxes, fats and derived compounds. Lipids are also known as lipin and lipoid. Lipids derive from animal fats and greases from fowl, fish or mammalian sources, oils from vegetables, seeds, or nut meat derivation.

Proteins: Proteins are found in animals, fish, fowl flesh, proteinaceous derivatives of fruits, vegetables, grains, nuts, and grasses.

Cellulose: Cellulose comprise digestible and indigestible fibers, fruit and vegetable skins, extractable coffee beans, tea leaves, bran, skins, chaff and stems from wheat, rice barley, or oats.

Pectin: Pectin is related to the starches of carbohydrates but water soluble; found chiefly in fruits and berries. Pectin gives jelly consistency and thickness. The pectic substances that are present in plant tissues, principally in fruits, are carbohydrate derivatives. Pectins or pectic substances are not soluble in water but, because of their highly hydrophilic colloidal nature, they disperse in water, readily forming a very viscous liquid. They also form a semisolid jelly with sugars and acids, and a semisolid gel with small amounts of bivalent ions. The high viscosity of the fruit juices is due to the presence of pectic substances that prevent the quick sedimentation of the dispersed particles.

Most organic waste comprise one or more of the following: fats, oils, greases, proteins and carbohydrates.

Enzymes

Enzymes are biologically produced catalysts which initiate a chemical reaction, speeding it up and enabling it to proceed under milder conditions, as at a lower temperature than otherwise possible, without entering into/or becoming a part of the reaction. Chemical reactions in biological systems rarely occur in the absence of a catalyst. Good enzymes retain their ability to catalyze many times. In our case, this becomes a method by which we measure their activity or the amount of work enzymes are capable of performing. The ability of enzymes to accelerate a reaction once started is also astonishing. All enzymes are catalysts composed of specific protein polymers. The main reaction enzymes initiate and cause to proceed to completion is hydrolysis. Hydrolytic enzymes hydrolyze or break up larger biopolymers into smaller units.

In the living cell, enzymes are provided as required by sequenced physiology within the cellular environment. When enzymes are extracted separately, and are not a part of a living cell, they perform their catalytic work according to precise laws and conditions. Enzymes, the natural linear polypeptides that catalyze biochemical reactions, have a mol wt of $10^5$–$10^6$. The single polypeptide chains of enzymes can aggregate in solution to yield molecular weights as high as several million. The weight of enzymes present per weight of biomass usually ranges from one tenth to one ten-thousandth part of the total biomass.

Enzymes, particularly industrially important enzymes, are known principally by their trivial (common, historical) names. These were given names based on the source of the enzyme by adding the suffix -in or -ain to a root indicating the source (eg, papain from papaya or pancreatin from pancreas), or named after the substrate or action by adding the suffix -ase to a root indicative of the substrate (eg, lactase acts on lactose, cellulase hydrolyzes cellulose, glucose oxidase oxidizes glucose).

Unlike other chemical entities, enzymes are characterized primarily on a functional basis. An enzyme is identified by what it does rather than its chemical composition. For example, a protein that speeds the decomposition of hydrogen peroxide to water and molecular oxygen is a catalase.

The enzyme molecule consists of a known chain of amino acids which has a particular geometric configuration specific for that arrangement of amino acids. The twisting and turning forms some locations that are catalytically active and these are referred to as the active sites.

The amount of enzyme affects only the rate at which equilibrium for the reaction catalyzed is reached. Most enzymes are highly specific and catalyze only one specific reaction or act upon only one isomer of a particular compound. Some enzymes are less specific and are able to catalyze several, usually related, reactions. The same reaction may be catalyzed by a large number of enzymes, different in their specific characteristics, and produced by different types of cells.

All enzymes are proteins, metalloproteins, or conjugated proteins. Metals are often an integral part of the enzyme, where separation can result in irreversible loss of activity (eg, $Fe^{3+}$ in catalase). In other cases, metal ions are required for activity or stability (eg, $Ca^{2+}$ for bacterial α-amylase). First of all, there are several enzymes whose activity depends on the presence of one or more thiol groups and which may be inactivated by the various reagents which can react with thiol groups, viz., by heavy metal ions or their derivatives (p-mercuribenzoate), by alkylating agents (iodoacetamide, etc.), and by oxidizing agents. These enzymes include papain, ficin, similar plant enzymes, certain cathepsins, and some bacterial and fungal proteinases. A second group includes those enzymes whose activity is dependent on bound metal ions, e.g., $Mg^{++}$, $Mn^{++}$, $Co^{++}$, $Zn^{++}$, $Fe^{++}$, and possibly others. A third distinct category of proteases includes those which are inhibited by diisopropyl phosphofluoridate (DFP) and similar organophosphorus compounds. These enzymes are not inhibited by thiol reagents or by metals. Some of the proteolytic enzymes in this group are trypsin, chymotrypsin subtilisin, and thrombin.

Generally, there are five generic hydrolytic enzymes that are capable of acting on the organic substances comprising 95%–98% of the sewage. Take the prefix of each and add the suffix "ase"—accordingly we have: amylase, lipase, protease, cellulase, and pectinase. Amylase hydrolyzes carbohydrates. Lipase hydrolyzes fats, oils and greases. Protease hydrolyzes proteins. Cellulase hydrolyzes cellulose. Pectinase hydrolyzes pectins and related water soluble gums.

Tetrazyme contains all of the functional ingredients for enzymes to perform effectively outside the living cell. In Tetrazyme, the technology has been developed and used to prevent denaturation of the multi-enzyme matrix system and to prevent protease from hydrolyzing it's companion enzymes.

Amylase:

Amylase is an enzyme that hydrolyzes carbohydrates, starch in plants and glycogen in animals.

α-amylase is more active in hydrolyzing larger molecules, cleaving them at random close to the middle of a long glucose chain. Glucoamylase splits off single glucose units, attacking at nonreducing ends of both long and short chains, and cleaves both (1–4) and (1–6) linkages. α-amylase, present in pancreas, saliva, plants, molds, and bacteria, hydrolyzes starch, glycogen, and dextrins. Some α-amylases of microbial origin are still active above 100° C. in the presence of substrate, whereas the malt β-amylase is rapidly destroyed above 63° C. α-amylase facilitates the action of other amylases.

Endoamylases act randomly on the α-1→4 linkages, through the α-1→6 bonds constituting the branching points of amylopectin and glycogen remain unattacked. This causes a rapid diminution of viscosity and average molecular weight of the substrate. Endoamylase comprise α-amylases, so called originally since the reducing hemiacetal group liberated by the hydrolysis is in the α optical configuration and mutarotates downward.

Most α-amylases can be obtained in the highly purified form. Crystallization can be obtained for the α-amylases of human saliva, human pancreas, hog pancreas, rat pancreas, Bacillus subtilis, Bacillus coagulans, oryzae, A. candidus, Pseudomonas saccharophila, and barley malt. α-amylases are all slightly acidic, water-soluble proteins of molecular weight around 50,000; they contain at least 1 gramatom of calcium per mole, which is essential for their activity; α-amylases differ from one another in several respects. Only mammalian and possibly some bacterial enzymes require chloride or other monovalent and possibly some bacterial enzymes require chloride or other monovalent anions for their activity.

Calcium is added during the purification of α-amylases, to stabilize the enzyme and also to promote its crystallization.

Crystalline α-amylases namely, human, porcine, bacterial, and fungal, remain fully active when incubated with large amounts of crystalline trypsin. Crystalline B. subtilis α-amylase can be exposed for prolonged periods of time to the separate action of a wide array of proteases, e.g., trypsin, chymotrypsin, subtilisin, pepsin, and papain, without undergoing any loss of activity.

Crystalline α-amylase from B. subtilis has a sedimentation constant is close to 6 S, which would correspond to a molecular weight of the order of 100,000, in contrast other α-amylases, which have molecular weights varying from 45,000 to 60,000. α-amylases are calcium metalloenzyme and therefore require $Ca^{++}$ ions for enzymic activity.

Amyloglucosidases comprises a saccharogenic amylase hydrolyzing starch, α-1, 4-oligosaccharide, and maltose to glucose. By a terminal or end-wise attack, single glucose residues are hydrolyzed from nonreducing chain ends. Amylo-1, 6-glucosidase (debranching enzyme) releases free glucose from phosphorylase and limit dextrins of glycogen or amylopectin with minimal action on undegraded polysaccharides.

Exoamylases are exclusively of vegetable or microbial origin. They are capable of attacking the polysaccharides only from the non-reducing outer chain ends and do so in a regular manner, breaking either every glucosidic bond to produce solely α-glucose, or every alternate bond to produce maltose. The former enzymes are called glucamylases or γamylases, and the latter β-amylases, since the maltose produced is found in the β-configuration. In both cases, the action stops at the first branching point, because the α-1→6 bonds are not split, and high-molecular-weight limit-dextrins are obtained. The saccharogenic amylase of malt has been classified as a β-amylase, on the basis of its ability to convert starch into the β-anomeric form of maltose. β-amylases attack alternate glycosidic bonds in normal starch chains, starting from the nonreducing end, continuing until the entire chain is converted into maltose or until further enzyme action is blocked by a physical or chemical irregularity in the chain. β-Amylase is principally found in germinating seeds (malt).

Glucoamylase (or amyloglucosidase) produces glucose by removing glucose molecules in succession from the nonreducing chain terminations from starch, glycogen, dextrins, and maltose molecules. It is present in blood, molds, and bacteria. Glucoamylase preparations are produced from molds. Amylo-1,6-α-glucosidase hydrolyzes (1–6)-α-linkages, the branching-off linkage in starch, glycogen, and dextrins. It is present in animal tissues, plants, yeast, and other microorganisms.

Human salivary α-amylase hydrolyzes α-1,4-glucosidic bonds in polyglucosans (amylose, amylopectin, glycogen, and dextrins). The initial stage of action of this enzyme is characterized by a rapid decrease of the molecular weight of the substrate.

Cellulase:

Cellulase are any of a group of extracellular enzymes, produced by various fungi, bacteria, insects and other lower animals that hydrolyze cellulose. Cellulase has a great economic potential for the hydrolysis of waste and other cellulosic materials to glucose. Cellulase performs well on cellulose derivatives, like carboxymethyl cellulose. Cellulases can be made from Aspergillus or Trichoderma viride. Cellulase has been purified from culture filtrates of Myrothecium verrucaria and crystallized from Irpex lacteus. Cellulose hydrolysis yields glucose and cellobiose. The enzyme also hydrolyzes carboxymethylcellulose.

Lipase:

Lipase is an enzyme that catalyzes the hydrolysis of fats or the breakdown of lipoproteins. Lipoproteins are any of a class of conjugated proteins consisting of a protein combined with a lipid. Lipases are esterases hydrolyzing esters of glycerol and fatty acids. Since fatty acids are attached to carbons 1, 2, and 3, the hydrolysis of a triglycerides results in the formation of a diglyceride, a monoglyceride, and finally glycerol as one, two and finally three fatty acid ester linkages are hydrolyzed. In the course of hydrolysis of a fat, at least three potential substrates exist: triglyceride, diglyceride, and monoglyceride.

Lipases show different affinities for these substrates. Pancreatic and Rhizopus arrhizus lipases substantially hydrolyze all of the triglyceride with accumulation of diglyceride before major attack on the diglyceride. Other lipases preferentially hydrolyze diglycerides or monoglycerides first.

Lipases show different affinities for esters with different chain lengths. Although pancreatic lipase shows greatest activity on long-chain fatty acid ($C_{12}$ or longer) chains, others such as pregastric lipases of young ruminants, act preferentially on short-chain fatty acid esters.

Lipase acts on tri-, di- and monoglycerides in decreasing order. Lipoprotein lipase, in contrast to pancreatic lipase, hydrolyzes fats in the form of lipoprotein. It has a high affinity for heparin. Pancreatin (pancreatic lipase) is useful in septic tanks and grease trap cleaners, and in removing tissue from hides destined for leather as enzyme-spotting agent for dry cleaners. Pancreatic lipase is almost always used as a crude dried pancreas powder blended with other materials. Proteolytic enzymes (e.g. trypsin and chymotrypsin) and amylases can be present. In addition to a high degree of emulsification, a number of other factors promote the hydrolysis of fats by pancreatic lipase. Cations, particularly $Na^+$ and $Ca^{++}$ promote lipolysis. Oil seeds (like soy, corn, castor) contain lipases that are important in the synthesis of the oils.

Olive oil is the most commonly used natural substrate for lipases. Calcium salts, either chlorides or lactates, can be added as activators. Pancreatic lipase is activated by cyanides and thio compounds.

Pectinase:

Pectinase are enzymes that catalyzes the transformation of pectin into sugar and galacturonic acid. Pectic enzymes take part in the hydrolytic degradation of pectic substances. The complete degradation of pectin requires a multiplicity of enzymes including esterases (pectin esterases) and glycosidases (pectinases). Pectinases are almost exclusively of vegetable and microbial origin, being found in bacteria and fungi, yeasts, and plants. Animal pectinases have been found in the digestive juice of the snails. Endopectinases have a high affinity for substrates of high molecular weight. Electrolytes can affect the activity of pectic enzymes. The pectic enzymes acting directly on pectic substances are comprised of three enzymes, of which polygalacturonase (PG) and pectin methylesterase esterase (PE), are hydrolytic, and pectate lyase or pectin transeliminase (PTE) is nonhydrolytic. Pectic enzyme preparations are fungal, from Aspergillus niger.

Pectinesterase also known as pectase, occurs in various plants and fungi. It hydrolyzes pectin one thousand times as fast as galacturonide esters. It is highly specific for polygalacturonide, where it seems to attack most readily methyl ester bonds adjacent to a free carboxyl group. It is more specific for the acyl than for the alkyl moiety.

Protease:

Proteases are enzymes that digests proteins. Proteases cause generation of free amino and carboxyl groups. Different types of proteases have been recognized by the chemical nature of their active sites. The substrates used for protease assay are both natural and synthetic; natural substrates are mainly milk casein, gelatin, and hemoglobin. The action of exopeptidases produces amino acids, whereas the endopeptidases produce peptides and peptones. Amino exopeptidases that attack the end with a free amino group whereas carboxy exopeptidases attack the end with the free carboxy group. Serine proteases are those inhibited by diisopropylfluorophosphate (DFP), and are all endopeptidases, including trypsin, elastase, chymotrypsin, and subtilisin.

Proteases include bacterial protease, mold protease and animal protease. Bacterial proteases include bacillus subtilis protease, streptoccal protease, pseudomonas protease, clostridium protease, and streptomyces protease. Mold proteases include aspergillus alkaline protease and aspergillus acid protease. Like animal enzymes, bacterial and mold proteases include enzymes which are active at acidic, neutral, and alkaline pH. The majority do not require activators, but some are activated by reducing agents and some by metal ions such as $Mn^{++}$, $Zn^{++}$, and $Co^{++}$, etc. The culture filtrates of Bacillus subtilis and similar bacteria are probably the richest and most convenient sources of bacterial protease for industrial use.

Plant proteases include papain. Papain is derived from the green fruit of Carica papaya. Papain tends to cleave the peptide at the arginine or lysine carbonyl group. Papain is used liquefying protein waste products and tooth-cleaning powders.

Bromelain (bromelin) is a plant protease manufactured from the hard stumps left after harvesting pineapples. Bromelain has properties and uses much like papain, except it is inactivated at a much lower temperature. Bacterial alkaline proteases Subtilisis derived from Bacillus licheniformis and other Bacillus species, can sometimes be useful in cleaning drains.

Proteases also include: acid proteases, alkaline proteases and neutral protease. The acid proteases include the milk-clotting enzymes used in cheese, pepsin from stomachs of adult pigs and cattle, rennin (rennet) from the stomachs of calves, and aspergillus acid protease. Acid proteases such as and some fungal amylases are active at pH 2–4. Alkaline proteases include aspergillus alkaline protease.

Neutral proteases are produced by both bacterial (Bacillus subtilis, Bacillus licheniformis) and fungal (Aspergillus sp.) sources in conjunction with acid or alkaline proteases.

Bacteria

The saprophytic bacteria contained in Tetrazyme are added to augment the flora on site sewage treatment systems normally develop. Further, in those systems in which the bacterial populations have been destroyed by misuse or addition of any matter that would eliminate it, the bacteria found in Tetrazyme, used on a regular maintenance basis, will function adequately until the normal saprogenic populations are reestablished.

Tetrazyme can contain saprophytic bacteria 200 million cells/gm, 5.6 billion cells/oz comprising the following genera and species: Bacillus subtilis, three strains, Bacillus licheniformis, Bacillus megaterium, Bacillus polymyxa. These bacterial strains have been chosen because under normal conditions found in on site disposal systems they will double their population density every 20 minutes. Furthermore, the three B. subtilis strains are excellent producers of amylolytic, proteolytic and cellulolytic enzymes.

The following bacteria genera, species and strains can be used because of their saprophytic waste-digesting ability, but are not preferred since they can be pathogenic. Two strains of Pseudomonas aeruginosa are excellent consumers of animal fats, grease, oil and petroleum hydrocarbons. Pseudomonas fluorescens biodegrades both hard and soft anionic, cationic, nonionic, and amphoferic detergents. Escherichia hermannii consumes cellulose and reduces sulfites.

Scavengers

Scavengers deactivate chlorine and heavy metals. Chlorine, a negatively charged ion (anion) and heavy metals, positively charged ions (cations), both adversely affect enzymes in a way that causes the enzyme to stop working. Both cause structural changes with in the enzyme causing it to fail to recognize and attach to the waste particle it is suppose to break apart. These changes in the actual shape of the enzyme caused by these negatively and positively charged ions is the reason why they need to be scavenged.

The component part of the Tetrazyme formulation that accomplishes this scavenging of the anions and cations is sodium thiosulfate (STS). By the same mechanism in which magnets attract metal filings, STS attracts both chlorine and heavy metals, called chelation. These chelated ions have now been tied-up, they have been made of no effect to the enzymes. The STS is ultimately utilized by the bacteria as an important source of sulfur for amino acid metabolism.

Formulation

As discussed above, Tetrazyme comprises the following:

Enzymes: amylase, cellulase, lipase, pectinase and protease.

Enzyme preservatives: Iso-octyl phenoldodecylethoxylate, nonylphenoldodecylethylate, Alpha dodecanoldecylethoxylate and/or alpha dodecanoldodecylethoxylate.

Enzyme Activators: Disodium phosphate and monosodium phosphate.

Bacterial Nutrients: Disodium phosphate, monosodium, phosphate, the enzyme preservatives and ultimately, the enzymes themselves.

Buffers: Disodium phosphate and monosodium phosphate.

Emulsifiers: same as the enzymes preservatives.

Heavy Metal Scavengers: Sodium Thiosulfate scavenges and inactivates chlorines and heavy metals so it doesn't chew up/deactivate enzymes.

The ranges of the above % by total weight of Tetrazyme are shown below:

| INGREDIENT | PRE-FERRED | INTER-MEDIATE | BROAD |
| --- | --- | --- | --- |
| Dendritic Salt | 70–90 | 60–90 | 50–95 |
| Protease | 0.25–0.50 | 0.10–5.0 | 0.10–15.0 |
| Surfonic N-95 | 2.0–7.0 | 1.0–10.0 | 1.0–20.0 |
| Amylase | 0.35–0.75 | 0.10–5.0 | 0.10–15.0 |
| Cellulase | 0.10–0.25 | 0.10–5.0 | 0.10–15.0 |
| Lipase | 0.15–0.25 | 0.10–5.0 | 0.10–15.0 |
| Bacterial Culture | 5.0–10.0 | 1.0–15.0 | 1.0–30.0 |
| Disodium Phosphate | 4.0–8.0 | 1.0–10.0 | 1.0–20.0 |
| Monosodium Phosphate | 2.0–4.0 | 1.0–10.0 | 1.0–20.0 |
| Sodium Thiosulfate | 1.0–2.0 | 0.10–5.0 | 0.10–10.0 |
| Lemon Scent | 0.10–0.50 | 0.10–2.0 | 0.10–5.0 |

Tetrazyme PC-108 can comprise the following:

Amylase 120,000 SU/gm 3,360,000u/oz

Cellulase 250 CMaseu/gm 7,000u/oz

Lipase 100TAu/gm 2,800u/oz

Protease 3,000 PCu/gm 84,000u/oz

Tetrazyme is non-poisonous, non-caustic, non-corrosive and biodegradable. Tetrazyme is preferably a blend of five enzymes; protease amylase, cellulase, pectinase and lipase along with aerobic and anaerobic nonpathogenic (harmless)

bacteria. Tetrazyme is desirable in that each ingredient is functional or contributes to the biodegration process. This scientifically blended product insures maximum results at lowest costs in the shortest time.

Septic System

A septic system is its own waste water facility. If operating efficiently, the waste water is discharged out the discharge pipes to the drainfield of gravel. The waste water then leaches out from the gravel and is purified through the soil. Failing septic tanks pose a potential health threat. Today's tough, stringent environmental standards require the replacement of many defective septic systems with new, undesirable and expensive-to-operate holding tanks.

Regular use of Tetrazyme waste digester and a regularly maintained schedule of pumping out a septic tank can prevent this problem effectively and economically. The use of Tetrazyme on a regular maintenance basis can markedly reduce the frequency of clean outs. The waste water from the system is ecologically acceptable and more readily cleansed by natural means. Tetrazyme improves the activity within the system to prevent clogged drains, grease trap over flow, septic tank flooding, clogged drain tiles and grease glazed drain fields.

Tetrazyme contains enzymes that convert protein and carbohydrate waste deposits into water soluble food for bacteria. Bacteria in the Tetrazyme digest food and produce natural grease liquefiers. Grease liquefiers break down fatty deposits. The bacteria in the Tetrazyme multiply and produce more enzymes that manufacture more food. Reproduction and digestion continue until all organic wastes are gone.

Tetrazyme works where bacteria products alone won't. Tetrazyme is ecologically desirable and has 100% active ingredients. Tetrazyme provides a natural aid to normal operation of waste disposal systems to increase their capacity for waste elimination. Tetrazyme also eliminates odors which attract insects. Tetrazyme substantially reduces gum and pectins which cause glazing of drain fields and drainage pits. Furthermore, Tetrazyme eliminates soggy soil and puddling due to clogging.

Use of Tetrazyme

Septic Systems, Cesspools and Dumping Stations. Use 2 oz. Tetrazyme PC-108NV per 1,000 gallons tank capacity once a week until system is operative. Troublesome systems will benefit from an initial shock treatment of 1 to 3 lbs. flushed down the drain or through the toilet. Then 2 oz. every two weeks as maintenance.

Drain Fields: For each 500 square feet of field, dilute 4 oz. of Tetrazyme PC-108NV with 10 gallons of warm water. Sprinkle or spray directly over tilled surface. An additional application can be made by adding 2 oz. to the distribution box between septic and field.

Drains: For slow drains, flush 2 oz. Tetrazyme PC-108NV with 1 cup luke warm water down drain. For best results apply at night when drain is not in use. Repeat once a week.

Grease Traps: One oz. of Tetrazyme PC-108NV mixed with warm water weekly. For best results use at night when trap is not in use. An initial shock treatment of 1–3 lbs. for residential use or 3–4 lbs. for commercial use may be required.

Recreational Vehicle (RV) Holding Tanks: Flush 2 oz. Tetrazyme PC-108NV and one gallon water into tank. Repeat after every dumping. Controls odors and facilitates pump out.

Garbage Disposes: 1 oz. of Tetrazyme PC-108NV with warm water. Allow to stand overnight. Repeat weekly.

Farms: To keep milk house drains open and odor free, follow directions for drains. To control animal waste odors and to facilitate manure clean-up in open house and cement floors, mix 4 oz. of Tetrazyme PC-108NV with 10 gallons of warm water, sprinkle or spray over area. Allow to stand 4 to 8 hours. Also controls odors in liquid manure holding tanks. Use only lukewarm water.

Municipal Sewage Treatment Plants: Sewage affluent will vary in quantity and quality in any given weekday and hour. The quality of the effluent leaving the plant will, in turn, depend on pH, temperature, biological activity and residence time. This being the case, it is best to adjust use of enzyme and bacteria activators to the mean or average of these variations. This is accomplished by titrating the system. This titration is best and most easily accomplished by performing the following steps:

1. Determine the average dried daily organic loading (on a daily basis) in pounds; (subtracting insolubles such as, twigs, sticks, gravel, pebbles, rags and similar refuse, i.e. all materials gathered before the affluent grit filters) for each put through residence time interval.

2. First week—use 1 pound of Tetrazyme PC-108NV for each 1,000 pounds of dry organic loading for each put through residence time interval.

3. Second week—use 1 pound of Tetrazyme PC-108NV for each 1,000 pounds of dry organic loading for each second put through residence time interval.

4. Third week—use 1 pound of Tetrazyme PC-108NV for each 1,000 pounds of dry organic loading for each third put through residence time interval.

5. Fourth week—use 1 pound of Tetrazyme PC-108NV for each 1,000 pounds of dry organic loading for each fourth put through residence time interval. Generally, more than four put through cycles used in 24 hours of less than 6 hours residence time, will overload the system.

6. Once optimum levels of Tetrazyme PC-108 have been determined by measuring total oxygen demand (TOD), dissolved solids (DS) and suspended solids (SS) at the effluent point; dissolve the total amount used at the lowest (minimum) level in sufficient water to input evenly into the affluent after grit filtering, but before primary settling, anaerobic digestion or grease scupper.

To determine total dry organic loading for each put through residence time interval, obtain triplicate 100 cc samples for each interval period. Filter through tared #4 Whatman filter, place filter paper with residue in a tapered Petri dish. Dry down for 24 hours in a 100° C. oven, weigh and record. Continue this daily for a seven (7) day period. Average the sums, divide by the number of samples. This will equal the average daily organic loading for a single day. Generally Desirably, Tetrazyme, also referred to as Tetrazyme PC-108NV, is non-poisonous, non-corrosive, and does not contain acids or lye. Tetrazyme is safe, non-toxic noncorrosive, non-polluting and orderless. Tetrazyme provides a stable powder multi-enzyme formulation which contains: amylase to hydrolyze starches, cellulase to hydrolyze paper and lipase to hydrolyze greases and oils into ecologically acceptable end products. Tetrazyme can be used to reduce grease trap cleanouts, as well as to clean and unplug sinks, drains, garbage disposals, plumbing, and floor drains. The regular use of Tetrazyme digests grease trap accumulation, prevents backup and overflows and greatly reduces the need for sludge removal. Inconvenience and operating costs are minimized. Tetrazyme converts waste into food for the natural bacteria found in an onsite sewage disposal system as well as the bacteria found in the product.

The preferred enzymes of the invention are particularly useful for the enzymatic degradation of household wastes in grease traps and septic tanks, and the acceleration of compost heap conversions. Tetrazyme provides a septic tank cleaner to speed the breakdown of household refuse entering the septic tank system. Septic tank treatment with Tetrazyme comprising amylase, protease, cellulase, lipase, pectinase, sequestrants, buffers, etc. can include viable organisms for the in situ synthesis of enzymes. Tetrazyme provides a grease trap cleaner for use in homes and restaurants. Grease trap cleaners can be reinforced with lipase. Cellulases speed the breakdown of grass clippings and other garden refuse in the compost heap. Immobilized cells (Canadida tropicalis or Psuedomonas sp.) degrade phenol and immobilized Micrococcus dentitrificans or Pseudomonas sp. can reduce the nitrate and nitrite content of waste waters.

Tetrazyme has no filler components. Each ingredient serves a purpose most effectively at its present concentration. This is exemplified most dramatically by the enzyme amounts. At present, a combined total of only 1.5% by weight proved to be a more effective product than a 26% enzyme amount with the added filler and at a significant savings per unit cost. In addition, some of the ingredients serve more than one function. The disodium phosphate and the monosodium phosphate function primarily as buffers and secondarily as enzyme activators and bacterial nutrients. The Surfonic N-95 functions primarily as an emulsifier and a bacterial nutrient. This multifunction aspect of the ingredients also decrease the volume of the raw materials inventory.

Tetrazyme provides an effective waste digestion composition. As discussed above, Tetrazyme comprises: an enzyme mixture; aerobic and anaerobic bacterial cultures; enzyme preservatives; bacterial nutrients; buffers; emulsifiers; and anion and cation scavengers. Desirably, complex compounds are degraded by Tetrazyme into simpler, less complex forms and eventually reduced to elements from which they originated.

Irrespective of the method used, e.g. thermal decomposition, biomassing as in landfills, municipal sewerage treatment or on site disposal, the desired outcome is liquification, cleanup and reduction in volume of the waste to environmentally acceptable material. The residue of this biodegradation is referred to as sludge in the liquid state and ash in the dry state. Periodically the accumulation of sludge can be removed by professionally trained septic system cleaners and disposed according to regulation of the Environmental Protection Agency or in other cases the Department of Natural Resources.

The use of Tetrazyme on a regular maintenance basis can markedly reduce the frequency of clean outs. Most importantly, Tetrazyme will improve the activity within the system to prevent clogged drains, grease trap overflow, septic tank flooding, clogged drain tiles, gum and grease glazed drain fields. Effluent from the treated system is ecologically acceptable and more readily cleansed as it percolates through the soil by natural means before reaching the aquifer.

Among the many advantages of the Tetrazyme technology of the invention are:

1. Superior cleanup of septic tanks, drains, drainage fields, garbage disposals and sinks.
2. Faster decomposition of compost heaps.
3. Outstanding product performance.
4. Ecologically safe.
5. Beneficial to the environment.
6. Easy to use.
7. Cost effective.
8. Superior quality.
9. Non-toxic.
10. Dependable.
11. Efficient.
12. Effective.

Although embodiments of the invention have been shown and described, it is to be understood that various modifications and substitutions, as well as rearrangements of parts, components, and process steps, can be made by those skilled in the art without departing from the novel spirit and scope of this invention.

What is claimed is:

1. A powdered composition for use in treating organic waste comprising:

multiple enzymes comprising less than 26% by weight of the total weight of the composition, said multiple enzymes comprising by weight
  from about 0.1% to about 15% protease;
  from about 0.1% to about 15% amylase;
  from about 0.1% to about 15% cellulase;
  from about 0.1% to about 15% lipase;
  from about 0.1% to about 15% bacterial culture selected from the group consisting of Bacillus subtilis, Bacillus licheniformis, Bacillus megaterium, and Bacillus polymyxa;
  from about 0.1% to about 20% disodium phosphate;
  from about 0.1% to about 15% monosodium phosphate;
said disodium phosphate and monosodium phosphate providing buffers;
  from about 1% to about 20% nonylphenoldecylethoxylate as an preservative;
  from about 0.1% to about 10% sodium thiosulfate as an ion scavenger; and
  from about 50% to about 95% dendritic salt providing a buffer.

2. The composition in accordance with claim 1 wherein said multiple enzymes further comprise from about 0.1% to about 15% pectinase.

3. The composition in accordance with claim 1 wherein said multiple enzymes comprise about 1.5% of the total weight of the composition.

4. A powdered composition for use in treating organic waste comprising by weight:

from about 50% to about 95% salts, said salts comprising from about 50% to about 95% dendritic salt, from about 1% to about 20% disodium phosphate, and from about 1% to about 20% monosodium phosphate;
from about 0.1% to about 15% protease;
from about 0.1% to about 15% amylase;
from about 0.1% to about 15% cellulase;
from about 0.1% to about 15% lipase;
from about 0.1% to about 15% pectinase;
from about 0.1% to about 15% saprophytic bacteria;
from about 0.1% to about 10% of an ion scavenger comprising sodium thiosulfate; and
from about 1% to about 20% of a non-ionic enzyme preservative selected from the group consisting of iso-octyl phenoldodecylethoxylate, nonylphenoldecylethoxylate, alpha dodecanoldecylethoxylate, and alpha dodecanoldodecylethoxylate.

5. A powdered composition for use in treating organic waste comprising by weight:

from about 60% to about 90% dendritic salt;

from about 0.1% to about 5% protease;

from about 0.1% to about 5% amylase;

from about 0.1% to about 5% cellulase;

from about 0.1% to about 5% lipase;

from about 0.1% to about 5% pectinase;

from about 1% to about 10% enzyme preservative selected from the group consisting of iso-octyl phenoldodecylethoxylate, nonylphenoldecylethoxylate, alpha dodecanoldecylethoxylate, and alpha dodecanoldodecylethoxylate;

from about 1% to about 10% disodium phosphate;

from about 1% to about 10% monosodium phosphate;

from about 0.1% to about 10% sodium thiosulfate; and from about 1% to about 15% nonpathogenic bacteria selected from the group consisting of aerobic bacteria, anaerobic bacteria, and combinations thereof.

6. The composition in accordance with claim 5 wherein the sodium thiosulfate is from about 1% to about 2%.

7. The composition in accordance with claim 5 comprising:

at least about 70% dendritic salt comprising sodium chloride;

from about 0.25% to about 0.5% protease;

from about 0.35% to about 0.75% amylase;

from about 0.1% to about 0.25% cellulase;

from about 0.1% to about 0.25% lipase;

from about 0.1% to about 0.25% pectinase;

from about 2% to about 7% a non-ionic enzyme preservative comprising nonylphenoldecylethoxylate;

from about 4% to about 8% disodium phosphate;

from about 2% to about 4% monosodium phosphate;

from about 0.1% to about 2% ion scavenger comprising sodium thiosulfate; and from about 5% to about 10% bacteria selected from the group consisting of Bacillus subtilis, Bacillus licheniformis, Bacillus megaterium, Bacillus polymyxa, and combinations thereof.

* * * * *